US011957806B2

(12) United States Patent
Sonovani

(10) Patent No.: US 11,957,806 B2
(45) Date of Patent: Apr. 16, 2024

(54) SYSTEMS, DEVICES AND METHODS FOR DISINFECTING OBJECTS OR SURFACES IN A SCENE

(71) Applicant: KILLER WHALE L.T.D., Tel Aviv (IL)

(72) Inventor: Binyamin Yefet Sonovani, Qatsrin (IL)

(73) Assignee: KILLER WHALE L.T.D., Tel Aviv (IL)

( * ) Notice: Subject to any disclaimer, the term of this patent is extended or adjusted under 35 U.S.C. 154(b) by 620 days.

(21) Appl. No.: 17/203,034

(22) Filed: Mar. 16, 2021

(65) Prior Publication Data
US 2021/0283293 A1 Sep. 16, 2021

Related U.S. Application Data

(60) Provisional application No. 62/989,971, filed on Mar. 16, 2020.

(51) Int. Cl.
*A61L 2/24* (2006.01)
*A61L 2/22* (2006.01)

(52) U.S. Cl.
CPC .................. *A61L 2/24* (2013.01); *A61L 2/22* (2013.01); *A61L 2202/14* (2013.01); *A61L 2202/15* (2013.01); *A61L 2202/16* (2013.01); *A61L 2202/17* (2013.01)

(58) Field of Classification Search
CPC .......... A61L 2/24; A61L 2/22; A61L 2202/14; A61L 2202/15; A61L 2202/16; A61L 2202/17; A61L 2/18
USPC ....................................................... 422/105
See application file for complete search history.

(56) References Cited

U.S. PATENT DOCUMENTS 10,492,023 B1 * 11/2019 Gurin .................... G06F 21/602
2015/0258234 A1 * 9/2015 Larsen ...................... A61L 9/04
422/4

\* cited by examiner

*Primary Examiner* — Huy Tram Nguyen
(74) *Attorney, Agent, or Firm* — Browdy and Neimark, PLLC

(57) ABSTRACT

There are provided methods, devices and systems for disinfecting one or more objects or surfaces in a scene comprising: a sensing subsystem, comprising at least one sensor configured and enabled to identify at least one user approaching the one or more objects or surfaces or the scene; at least one device for measuring a distance of said at least one user or said one or more objects and at least one timer for measuring the time said at least user or said one or more objects are in the scene; a treatment subsystem, comprising: one or more containers comprising cleaning or disinfecting agents or materials; at least one pump and one or more spraying devices and a processing subsystem comprising at least one processor, configured to activate the one or more spraying devices before or after the identified one or more users touch the one or more objects or surfaces or approach or leave the scene.

20 Claims, 9 Drawing Sheets

SYSTEMS, DEVICES AND METHODS FOR DISINFECTING OBJECTS OR SURFACES IN A SCENE

CROSS-REFERENCE

The present application claims the benefit of U.S. Provisional Application Ser. No. 62/989,971 filed on Mar. 16, 2020, entitled "SYSTEMS, DEVICES AND METHODS FOR DISINFECTING OBJECTS OR SURFACES IN A SCENE" which is incorporated herein by reference in its entirety.

TECHNICAL FIELD

The present invention, in some embodiments thereof, relates to systems devices and methods for disinfecting or cleaning objects or surfaces in a scene, more specifically, but not exclusively, to systems devices and methods configured to automatically or autonomously sterilizing or disinfecting or cleaning objects or surfaces in a scene.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Sterilization and disinfection are necessary for the destruction or removal of all microorganisms (including spore-forming and non-spore-forming bacteria, viruses, fungi, and protozoa and pathogen (anything that can produce disease), etc.) that could contaminate pharmaceuticals or other materials and thereby constitute a health hazard.

Disinfection and sterilization are also essential for ensuring that objects such as medical and surgical instruments do not transmit infectious pathogens to patients. Today many health-care policies must identify, primarily based on the items' intended use, whether cleaning, disinfection, or sterilization is indicated.

SUMMARY OF THE INVENTION

According to some aspects, there is provided a system for disinfecting one or more objects or surfaces in a scene, the system comprising: a sensing subsystem, the sensing subsystem comprising: at least one sensor configured and enabled to identify at least one user approaching the one or more objects or surfaces or the scene; at least one device for measuring a distance of said at least one user or said one or more objects or surfaces from the system; at least one timer for measuring the time said at least user or said one or more objects are in the scene or touching the one or more objects or surfaces; a treatment subsystem, said treatment subsystem comprising: one or more containers comprising cleaning or disinfecting agents or materials; at least one pump connected via one or more pipes to the one or more containers said at least one pump is configured and enabled to pump said cleaning or disinfecting agents or materials to one or more spraying devices, wherein said one or more spraying devices comprising one or more nozzles for spraying the one or more objects on the scene or on the one or more objects or surfaces in the scene; a processing subsystem comprising at least one processor, said at least one processor is configured to: receive said identification of the at least one user approaching the one or more objects or surfaces or the scene; activate the one or more spraying devices before or after the identified one or more users touch the one or more objects or surfaces or approach or leave the scene based on the measured time or identification or location or measured distance of the one or more users from the system.

In an embodiment, the at least one sensor is configured and enabled to capture sensory data of the scene and wherein the processing subsystem is configured to: analyze the captured sensory data, using one or more machine learning or network neural methods to yield detailed information on the scene; and accordingly activate or deactivate the one or more spraying devices.

In an embodiment, the detailed information comprises one or more of: measuring the number of the one or more users approaching or in proximity to the one or more objects or surfaces in the scene or leaving the scene; the time the one or more users are at the scene; classification of the users; the type and amount of the identified bacterium.

In an embodiment, the system comprising a scheduler wherein the scheduler is configured to schedule and activate the treatment subsystem based on the measured time or number of the one or more users identified in the scene or touching objects or surfaces in the scene or approaching or in proximity to the one or more objects or surfaces in the scene.

In an embodiment, the sensing subsystem comprises an illumination subsystem comprising at least one illumination source configured to illuminate the scene.

In an embodiment, said one or more nozzles are fog nozzles.

In an embodiment, the spraying devices may be positioned externally to or in the treatment subsystem and wherein the nozzles are configured to rotate in perpendicular to the treatment module length.

In an embodiment, the cleaning or disinfecting agents or materials are in the form of liquid or gas or any other aggregate state.

In an embodiment, the sensory data comprise one or more images of the scene.

In an embodiment, the disinfection or cleaning may be automatically or autonomously be operated every hour or according to predefined time intervals or upon specific requests.

In an embodiment, the sensing subsystem may include one or more sensors selected from the group consisting of: proximity sensors; pressure sensors for detecting a movement of a user at the system's vicinity and accordingly activating or deactivating the system; RF sensors, IR sensors, pressure sensors, laser sensors.

In an embodiment, the system comprising a communication circuitry to couple to the system and communicate with a remote server, and wherein the processing subsystem comprising instructions to transmit the sensory data to the remote server.

In an embodiment, the sensory data comprises one or more of an identification of the one or more objects, a classification of the one or more objects among a plurality of classifications, one or more components the one or more objects.

In an embodiment, the treatment subsystem comprises at least one robotic arm.

In an embodiment, the system comprising a power source.

In an embodiment, the system comprises one or more motors for enabling the system to move in the scene or fly in the scene.

In an embodiment, the system is attached to a mobile system said mobile system comprising a motor configured to move the system.

In an embodiment, the system is attached to a drone or a vehicle.

In an embodiment, the system comprises one or more electronic faucet for controlling the quantity and timing of a disinfection process.

In an embodiment, the treatment subsystem is activated according to a cleaning matrix, said cleaning matrix comprises cleaning procedures and wherein the cleaning matrix is based on the processed sensory data.

BRIEF DESCRIPTION OF THE DRAWINGS

A better understanding of the features and advantages of the present disclosure will be obtained by reference to the following detailed description that sets forth illustrative embodiments, in which the principles of embodiments of the present disclosure are utilized, and the accompanying drawings.

DETAILED DESCRIPTION OF THE INVENTION

Figure 1A:
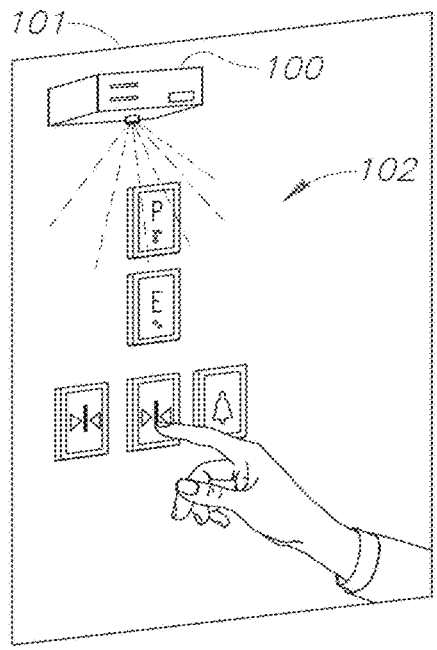
FIGS. 1A-1D show various views of systems configured and enabled to automatically and/or autonomously sanitize or clean or disinfect one or more objects or surfaces in a scene such as the objects' surfaces or one or more buttons of the object, in accordance with some embodiments of the present disclosure.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

The configurations disclosed herein can be combined in one or more of many ways to provide improved cleaning and/or disinfection methods, systems and devices. One or more components of the configurations disclosed herein can be combined with each other in many ways. Devices, systems and methods as described herein including a system comprising a sensing subsystem configured and enabled to sense one or more users, for example, using or holding or touching one or more objects or surfaces in a scene and automatically and/or autonomously clean or sanitize the identified objects and/or the objects' surfaces and/or surfaces in the scene by spraying cleaning or sanitization materials on the objects and/or the objects' surfaces and/or surfaces and/or the scene.

According to one embodiment, the sensing subsystem comprises one or more sensors configured to capture data (e.g. sensory data) of one or more scenes such as the surrounding environment where the system is located and a processing subsystem comprising one or more processors configured to receive the data and analyze the captured data to yield detailed information of the one or more scenes. In some cases, the detailed information may include the type of the one or more scenes (e.g. kitchen, ATM, etc.) users, number of users, and/or attribution of the one or more scenes, classification of the one or more objects or users, location and/or position and/or the type of use of the one or more users, and/or time spent in the scene, and/or direction and/or distance from the system and accordingly clean the scene and/or objects for optimally and accurately disinfect the scene and further learn the characteristic of the identified objects and one or more users in the scene. In some cases, the detailed information identified by the processors may include the type of use of one or more users and accordingly clean the scene and/or objects for optimally and accurately disinfect the scene. In some cases, the detailed information may be shared for example by transmitting the detailed information to one or more storage units of an information library, located for example in a remote server (e.g. cloud-based server). The information in the library may be further shared by other devices.

According to some embodiments, the system comprises a sensing subsystem, comprising at least one sensor configured to acquire sensory data of the scene; an illumination unit comprising at least one illumination source configured to illuminate the scene; a processing subsystem comprising at least one processor configured to receive and analyze the acquired sensory data, using one or more machine learning (ML) or network neural or artificial intelligence (AI) methods to identify one or more objects and/or users in the scene and further yield detailed information (e.g. complete and detailed processed data) of the scene, wherein the detailed information may include one or more of identification of one or more object and/or the attributes of one or more objects in the scene or their way of operation over time; and a treatment subsystem comprising one or more spraying devices configured and enabled to sanitize or clean the identified one or more objects and/or surfaces in the scene based on the processed data.

According to some embodiments, the sensing subsystem comprises at least one device for measuring a distance of the at least one user or the one or more objects or surfaces from the system, for example continually over time.

According to some embodiments, the sensing subsystem comprises at least one timer for measuring the time the at least user or the one or more objects are in the scene or touching the one or more objects or surfaces;

According to some embodiments, the AI or ML methods may include one or more Jabberwacky artificial intelligence chat robot, AIML LISP, Boltzmann Machines methods. In some cases, the cleaning procedure may be based on a predefined cleaning checklist.

According to some embodiments, there is provided a system for cleaning and/or disinfecting one or more objects or surfaces in a scene, the system comprising: a sensing subsystem, comprising at least one sensor configured to capture sensory data of the scene; an illumination device comprising at least one illumination source configured to illuminate the scene; a processing subsystem comprising at least one processor configured to analyze the captured sensory data, using one or more machine learning and/or network neural methods and/or AI methods to identify one or more users approaching/leaving the scene or in proximity to the one or more objects or surfaces; and a treatment subsystem comprising: one or more containers comprising cleaning or disinfecting agents and materials; one or more spraying devices comprising one or more nozzles configured and enabled to disinfect the one or more objects before and/or the identified one or more users touch or approach the one or more objects or surfaces in the scene.

According to one embodiment, the treatment subsystem comprises at least one pump connected via one or more pipes to the one or more containers, wherein the at least one pump is configured and enabled to pump the cleaning or disinfecting agents or materials to the one or more spraying devices, wherein said one or more spraying devices comprising one or more nozzles for spraying the one or more objects on the scene or on the one or more objects or surfaces in the scene.

Alternatively or in combination, the system may include communication circuitry to couple to the system and communicate with a remote server, and wherein the processing subsystem comprising instructions to transmit the complete and detailed data to the remote server.

According to some embodiments, the data can be made available to users and non-users in many ways, for example with downloadable apps capable of connecting to the cloud-based server and downloading information related to the captured scene and/or to one or more objects in the scene.

According to some embodiments, the system and methods are configured to autonomously and/or automatically disinfect and/or clean one or more surfaces such as selected surfaces in a scene 24/7 without human hand contact.

Overview of Sanitization Systems and Methods

FIGS. 1A-1D show various views of system 100 configured and enabled to automatically and/or autonomously sanitize or clean or disinfect a scene or one or more objects or surfaces of devices or systems in the scene, such as the objects' or devices' surfaces or one or more buttons of the object or device, in accordance with embodiments. For example, as shown in FIG. 1A system 100 is configured to disinfect an elevator's buttons 102 and/or any surface 101 in the elevator space at any selected or predefined time. In another example, shown in FIG. 1B system 100 is configured to disinfect the buttons or touch screen surface of an Automatic Teller Machine (ATM) 104 and/or any surface in the ATM space at any selected or predefined time. In some cases, the system may measure the distance 'd' of the user 103 from the ATM 104 and/or the time user spends near or pressing the ATM and accordingly match an appropriate cleaning or disinfecting process, e.g. type of cleaning materials, cleaning or disinfecting time duration, and/or the number of cleaning cycles. In yet another example, shown in FIG. 1C the system 100 is configured to disinfect and/or clean on/off electric switches 107 in a room or office at any time, for example, based on the identified measured number of users, or classified users which touched the switches or the time the users spent in the room. Another example, shown in FIG. 1D includes disinfecting and generating an appropriate cleaning or disinfecting process, e.g. type of cleaning materials, cleaning or disinfecting time duration, and/or number of cleaning cycles of the faucet 109 and/or faucet handles 109' or sink 109" or any touch surfaces or spaces in a room such as an office or kitchen any time and/or according to the measured number of users which were identified using or touching the faucet and/or faucet handles or any touch surface or space in the room.

In some embodiments, the system may include or may be attached to a drone 111 or to any type of aerial vehicles such as unmanned aerial vehicle (UAV) which may automatically and/or autonomously fly near and/or above the object for optimally clean or disinfect the object or the scene based in instructions received from the processing subsystem.

Other examples of objects and/or surfaces which system 100 is configured to automatically and/or autonomously clean and/or sanitize include one or more of: handles of all types such as closet or drawer handles; car steering wheel; handrail; escalator handrail, bus or train columns; toilet water handle; automatic bank buttons; vending machines; supermarket products, unprocessed food, various packaging, Mail packs, packages in general; cell phones; work surfaces; work surfaces; keyboards; toys, pillows; room parts; utensils; Utensils; car spaces; public vehicle; cash register; box office tickets; toilets such as toilet flash tank; electronic switches; biometric surfaces; signature pads (e.g. for credit payment); ATM; and the like.

According to some embodiments, system 100 may be included or embedded on the various devices, for example, embedded in the ATM or in the elevator.

Figure 1B:
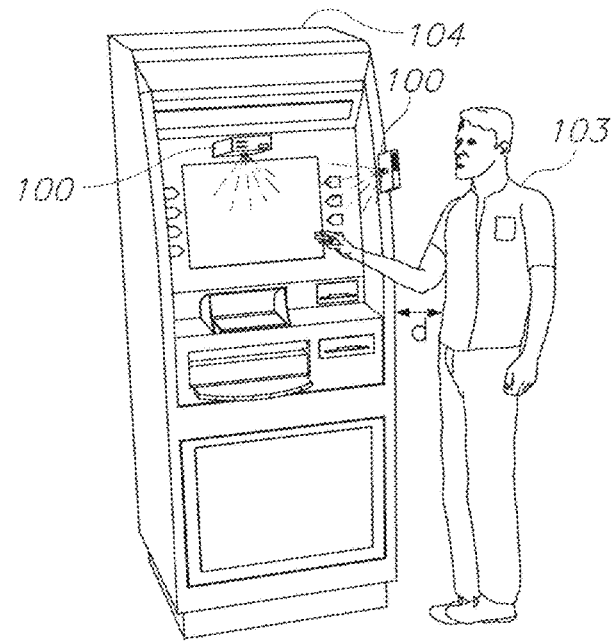
Figure 1C:
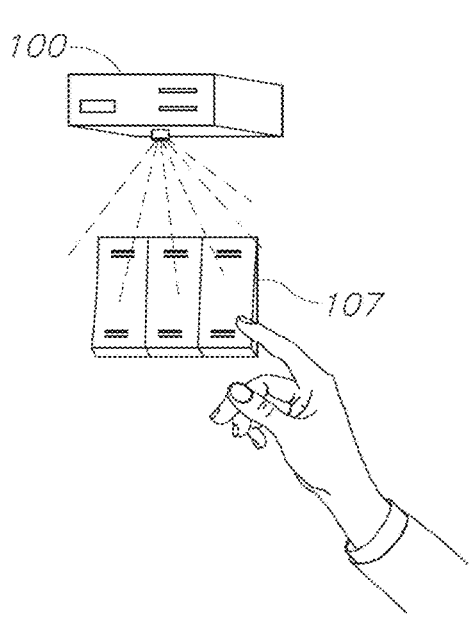
Figure 1D:
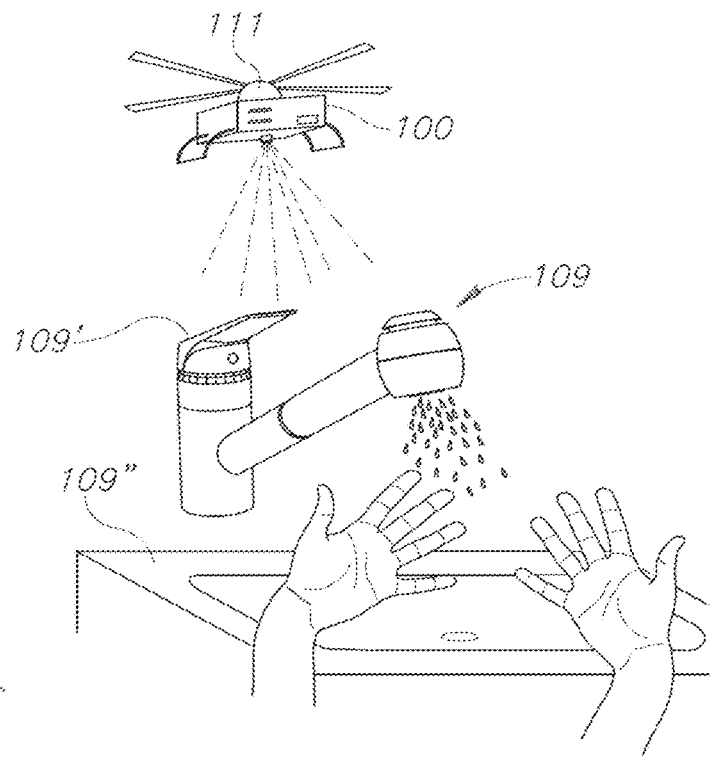
Figure 1E:
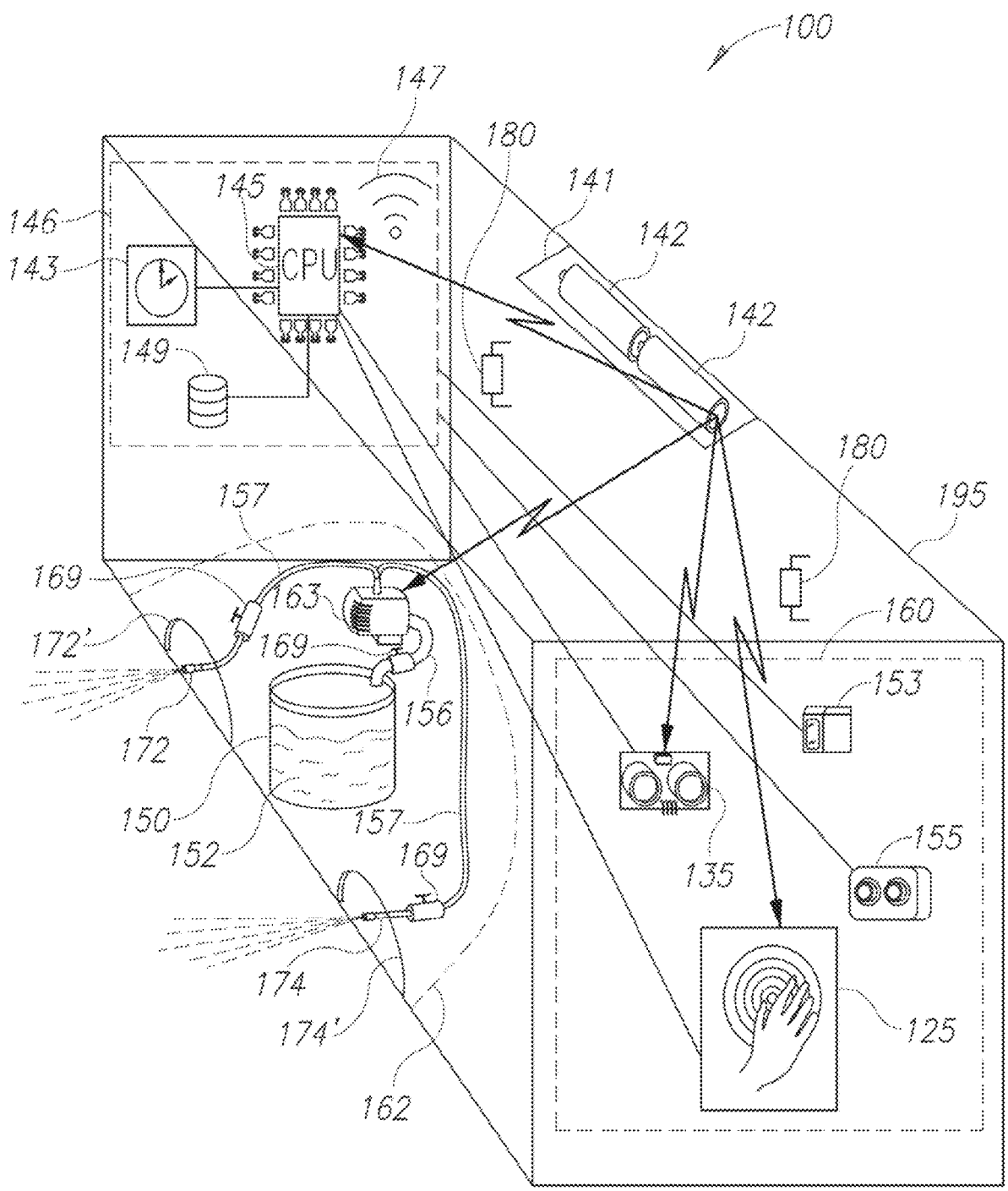
FIG. 1E shows a schematic side view of a system for automatically and/or autonomously sanitize or clean or disinfect one or more objects or surfaces in a scene, in accordance with some embodiments of the present disclosure.

FIG. 1E shows a schematic side view of the system 100 in accordance with embodiments. System 100 may include a processing and control subsystem 146, a treatment subsystem 162 a sensing subsystem 160. The sensing subsystem 160 may include one or more sensors such as a proximity sensor 125. In some cases, another type of sensors may be used such as a pressure sensor or other sensors as listed in FIG. 3.

In some cases, the sensing subsystem may include one or more of temperature sensors; motion sensors; optical sensors; biological sensors; radar sensors; acidity sensors; light sensors; humidity sensors; air sensors; gas sensors sound sensors, and the like.

In some cases, the sensors may be sensors of Interlink Electronics FSR™ 400 series. The sensors may include Force Sensing Resistors or FSRs. The sensor may be a round sensor 18.28 mm in diameter.

In some cases, the proximity or motion sensor may be HC-SR505 Mini PIR motion sensor or other known motion sensors which are based on infrared technology and may automatically control by itself with high sensitivity and high reliability (see for example http://www.elecrow.com/hcsr505-mini-pir-motion-sensor-p-1382.html)

Optionally, the sensing subsystem 160 may include one or more illuminators (e.g., laser transmitter 135) such as an infra-red (IR) pattern illuminator and a camera 155 such as an IR camera or an image camera or a stereoscopic camera.

Optionally, system 100 may include at least one device for measuring the distance 'd' of at least one user from the system or the one or more objects or surfaces in the scene. In some cases, the device may be a laser distance meter 153 used for accurately determining the distance of one or more users approaching or going away from the system or from the objects or surfaces at the scene. In some cases, the distance may be obtained by measuring the transit time of laser pulses between the laser distance meter and the object to be measured. The distance measurements may be continually obtained over time and transmitted to the processing subsystem for activating the treatment subsystem before and/or after one or more users were identified.

According to some embodiments, one or more sensors such as proximity sensors and/or pressure sensors are used for detecting a movement of one or more users at the system's vicinity (e.g. 0-10 meters) and accordingly activating or deactivating the system. In some cases, the system may include RF sensors, IR sensors, pressure sensors, laser sensors. In some cases, the sensors may be sensors configured and enabled to detect the smell (e.g. 0-10 meters) in proximity to the device.

In some cases, the users or objects in the scene may be identified in a range of 1, 2, 3, 4-10 mm from the system and/or up to 10 meters and more from the system.

According to one embodiment, the storage and treatment subsystem 162 may include one or more storage devices and one or more cleaning and spraying devices The one or more storage devices may be or may include one or more containers, for example, container 150 configured to store treatment material such as detergents and/or cleaning and/or disinfecting agents and materials and/or a chemical mixture such as specific cleaning and disinfection formulas; propanol, n-Propanol, Aldehydes and the like.

The one or more spraying devices may be or may include one or more nozzles configured to spray the cleaning materials on the objects and/or on the object's surface typically on a wide and large area of the objects and/or the surfaces.

According to one embodiment, the spraying devices may include one or more nozzles such as nozzles 172 and 174 which are configured to receive cleaning treatments such as cleaning or disinfection detergents of a chemical mixture from the container. The chemical mixture is then sprayed for example automatically on the object (e.g. on the object's surface such as buttons).

According to some embodiments, one or more spraying devices are shaped for example as an elongated pipe. In some cases, the spraying devices may be positioned externally to or in the system 100 and are configured to rotate perpendicular to the treatment module length. In some cases, the spraying devices are configured to deliver and disperse cleaning material, such as materials including sanitization agents from container 150 and spray automatically and/or autonomously the materials on the one or more objects or surfaces.

In some cases, container 150 may store cleaning materials or compositions such as deodorizing and disinfecting materials (e.g. detergents) which may be dispensed by the spraying devices on the objects.

In some cases, the disinfectant materials may be in the form of liquid or gas or any other aggregate state.

In some cases, the materials (e.g. disinfectant materials) may be stored in pressure tanks and/or in one or more containers comprising an electrical or mechanical pump, or chemical pumps, and/or any other means for generating pressure configurable to deliver the disinfectant materials to the identified objects or surfaces which require cleaning or disinfection.

For example, the treatment subsystem 162 may comprise one or more pumps such as a liquid pump 163 for pumping material 152 via pipe 156 and pipes 157 from the container 150 to one or more nuzzles such as nuzzles 172 and 174 for spraying the material 152 via one or more openings 172' and 174' to selected points on one or more objects or surfaces which need to be cleaned and/or disinfected as shown in FIGS. 1A-1D.

According to some embodiments, the nozzles 172 and 174 may be with or without an arm such as a mechanical or a robotic spraying arm.

According to some embodiments, the nozzles 172 and 174 may be fog nozzles or any type of nozzles as known in the art.

In accordance with embodiments, the processing subsystems 146 includes one or more processors such as processor 145 (e.g. CPU) for processing data such as sensory data captured by the one or more sensors of the system and/or external sensors which are in communication with the system 100 and/or external devices such as computer devices or smart mobile phone devices or the like. Based on obtained data and processed data the one or more processors are configured to operate and control the system units, and subsystems such as the spraying devices.

In some cases, processor 145 can execute a sequence of machine-readable instructions, which can be embodied in a program or software. The instructions may be stored in memory 149.

In some cases, system 100 may include one or more timers or schedulers such as scheduler 143 for scheduling the cleaning and/or disinfection process of the objects or surfaces (e.g. activating and deactivating the systems' units, such as one or more spraying units) according to predefined time intervals and/or based on data (e.g. processed sensory data) received from the processor 145.

In accordance with embodiments, scheduler 143 is configured to schedule the cleaning and/or disinfection process of the objects or surfaces. In some cases, the scheduler 143 may comprise predefined fixed time or according to the type of use and/or the number of people who used the object and/or the classification of the users (e.g. general users/maintenance workers) and/or the type and amount of the identified bacterium. For example, in the case of a vehicle's steering wheel, the cleaning and/or disinfection process is scheduled based on the identified user and or occupancy state of the vehicle, while for the ATM in working hours where many people touch the ATM screen the cleaning cycles are scheduled frequently (every 10, 20, 30, 40 50 seconds) while on the night, once each hour.

In some cases, scheduler 143 is configured to 'open' and 'close' the spraying devices based on information received from the processors and/sensors. For example, in cases where the proximity sensor 125 or the distance sensors identify prolonged presence of one or more users at the scene or touching/pressing the objects or the surfaces or elements on the surface, the scheduler 143 will activate an intensive and long cleaning and disinfection process of the scene and objects in the scene, while in cases the sensor identified short time and single use the scheduler will initiate a short cleaning and disinfection process or cycles.

In some embodiments, system 100 comprises one or more electronic faucets such as one or more electronic faucets 169

(e.g. stopcock) for controlling the quantity and timing of the disinfection process. The electronic faucet 169 may be equipped with a proximity sensor or may be in communication with the proximity sensor 125 and/or any other sensor. The electronic faucet 169 includes a mechanism that opens its valve, for example upon a received instruction from the processing ad control subsystem 146, to allow liquid and/or odor or any type of material to flow in response to the presence of a user such as a hand or hands in proximity, for example, 1, 2, 3, 4, 5, 6, 7, 8, 9, 10 or more cm from the object or from the system. The electronic faucet 169 closes its valve again after a few seconds or when the sensors no longer detect the presence of hands or when it receives an instruction for example from the processing and control subsystem (e.g. processor 145 or scheduler 143). In some embodiments, the faucets may be battery powered and incorporate an active infrared sensor to detect motion.

In some cases, the scheduler 143 may be or may be included in the control and processing subsystem 146 and for example, may be connected or in communication with the processor 145.

In many embodiments, the system 100 may be in communication with the remote server which may be a centralized cloud-based server configured to receive data such as sensory data from millions of devices and analyze the data. In many cases, the cloud base server is configured to transmit data, including for example analysis results, to the millions of devices or systems such as system 100 for example in response to one or more specific requests.

In some embodiments, a communication circuitry 147 for communicating for example with a remote server may be included in the processing subsystem 146.

According to many embodiments, the system 100 may include power source 141 including for example one or more batteries 142. Alternatively or in combination, system 100 may include a portable power source. In some cases, the system 100 may be connected to an external power source via one or more connection ports such as USB connection ports. For example, the system may be connected to a vehicle's power source or to a power outlet of a building or an elevator or to a solar panel or the like at the scene where the cleaning and/or disinfection process is required. In some cases, the power source may be a solar power source or based on solar power sources. In some cases, the power source may be a dynamo power source.

In some cases, all or some of system devices or units such as the processing subsystem 146, a treatment subsystem 162 a sensing subsystem 160 may be included within a housing 195 such as a case or box configured to be attached to one or more surfaces for example in proximity to devices, systems, objects or any element which need to be cleaned and disinfected from time to time.

According to some embodiments, system 100 may be modular including the treatment module the sensing module and the storage and control module.

In some cases, the treatment subsystem, the sensing subsystem and processing subsystem are formed and connected as one piece, alternatively, the treatment subsystem and processing subsystem are formed or connected as one piece via a connection device that is connectable to the sensing subsystem.

In many cases, the processed sensory data may be encrypted and/or compressed. Once encrypted, the compressed encrypted data can be transmitted via wireless communication such as Bluetooth or WiFi or other wireless protocols to other systems and devices.

In some embodiments, system 100 includes one or more monitors for generating one or more alerts on the condition and amount of material of the system and/or the sanitization and cleaning status of the objects or any information required.

According to one embodiment, the system may comprise one or more attachment units 180 for coupling the system 100 to or near the object or surface which requires cleaning and/or disinfection. The attachment units 180 may be or may include one or more linkage materials such as a mechanical attachment or glue or screw magnet, static electricity, electrical or chemical or biological mechanical connection, and the like. The linkage module is configured to be attached to the object or surfaces which require disinfection.

In operation, system 100 identifies one or more users such as users in a scene using or activation one or more devices or objects and/or pressing buttons for example for a few seconds or in predefined intervals. Following the identification of one or more users and/or contaminated scene the system disinfects and/or cleans the related one or more objects or surfaces and/or the scene. In some cases, the disinfection and/or cleaning may be performed before or following the user's use of or touching these objects. In some cases, the disinfection and/or cleaning may be automatically or autonomously operated every hour and/or according to predefined time intervals and/or upon specific request. In some cases, the disinfection and/or cleaning may be repeated and include one or more cleaning or disinfecting cycles until complete and optimal disinfection and/or cleaning is accomplished.

According to other embodiments, the system 100 is configured to identify (e.g. using for example the sensing subsystem 160) one or more users approaching and/or drawing away from an object or surface (e.g., for example, the system may identify one or more users entering an elevator or an ATM as respectively illustrated in FIG. 1A and FIG. 1B) and immediately disinfection and/or cleaning process is initiated before the one or more users touch and/or use the objects. At the following step, once one or more users were identified leaving the area (e.g. the objects or surfaces, for example leaving the elevator or the ATM) the disinfection and/or cleaning process is repeated.

In cases where many users use or touch the objects, the system may automatically initiate a disinfection and/or cleaning process every predefined time interval.

Figure 2:
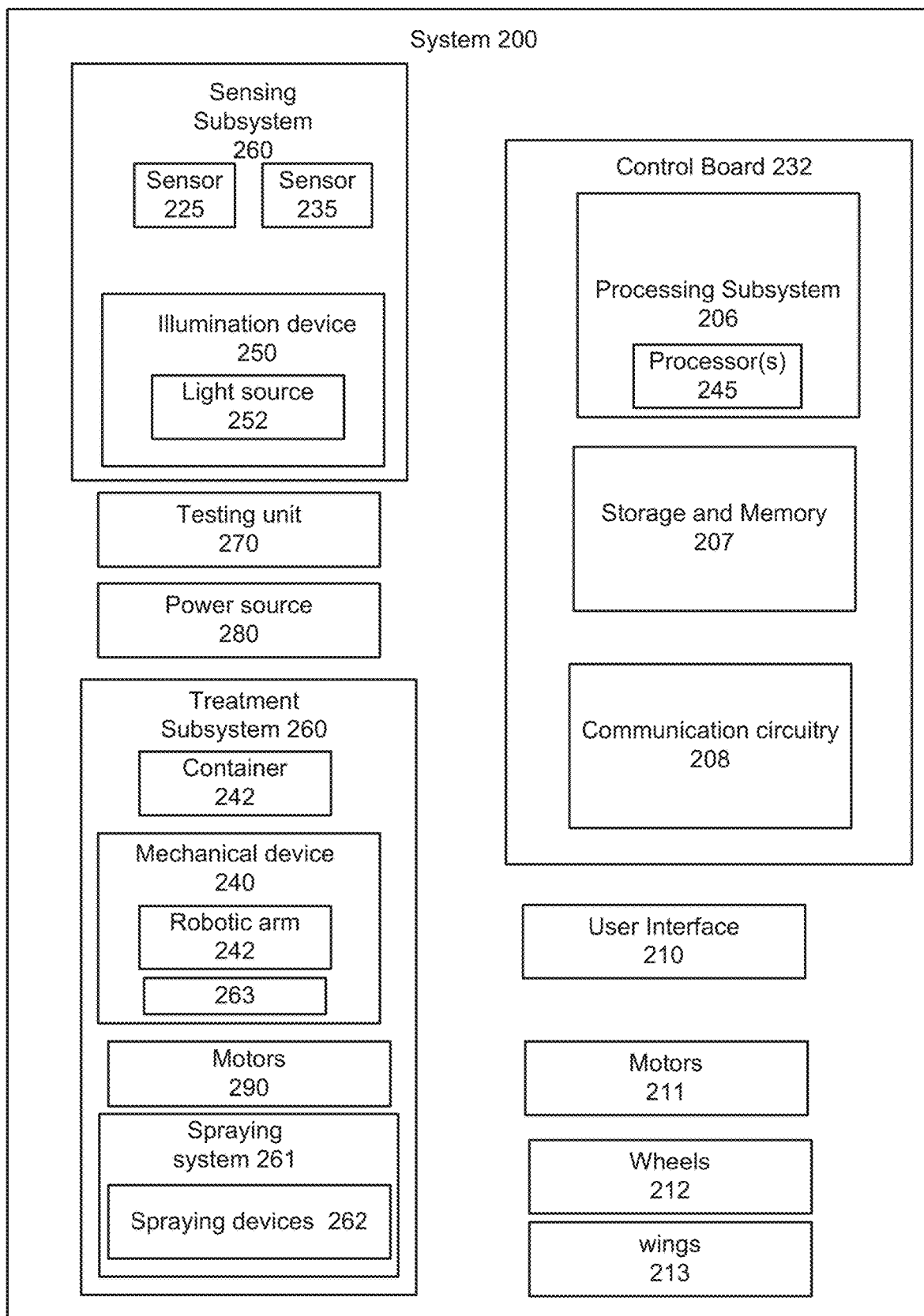
FIG. 2 shows a block diagram of a system for automatically and/or autonomously sanitize or clean or disinfect one or more objects or surfaces in a scene, in accordance with some embodiments of the present disclosure.

In some cases, the system may identify the number of users and/or time the number of users used or touched objects or devices or the amount (e.g. size and quantity) of contamination in the scene and accordingly match a cleaning procedure based on the identified FIG. 2 shows a schematic detailed diagram of a system 100 such as a cleaning system, in accordance with embodiments. In some cases, system 200 may be system 100 of FIG. 1E or may include all or some elements of system 100, in accordance with embodiments. System 200 comprises a sensing subsystem 260 and illumination device 250 which together can be configured to obtain sensory data and measure information relating to one or more objects in a scene. Specifically, the sensing subsystem 260 is configured and enabled to obtain data such as sensory data of a scene and objects in the scene, such as data relating to objects 102, 104, 107 and 109, and/or for example, one or more users approaching or leaving the scene or in proximity to the objects in the scene, or for identifying bacterium or any elements that need to be cleaned using one or more sensors such as sensors 225 and 235 as shown in FIGS. 1A-1D. The illumination device 250 is configured and enabled to project light to the scene.

The system 200 may further comprise a mechanical device 240 and a control board 232. The control board 232 may comprise one or more of a processing subsystem 206, communication circuitry 208, and memory 207. Components of the control board 232 can be configured to transmit, store, and/or analyze data, as described in further detail herein.

The processing subsystem 206 may comprise one or more processors 245 including a tangible medium comprising instructions of a computer program; for example, the one or more processors 245 may comprise a digital signal processing subsystem, which can be configured to analyze the obtained sensory data of the scene using learning methods and/or neural networks and output complete and detailed data of the scene for identifying attributes and the way of operation of the objects in the scene.

According to some embodiments, the obtained sensory data may be analyzed using one or more of the following methods Independent Components Analysis (ICA), (LDA) analysis, wavelets G and the like.

According to some embodiments, the sensory data is analyzed to identify the number of users in the scene, and further yield data relating to the one or more users including for example: location and/or position and/or orientation and/or the type of use of the one or more users, and/or time spent in the scene, and/or direction, distance from the system and accordingly clean the scene and/or objects for optimally and accurately disinfect the scene.

Specifically, for optimally cleaning the scene the type and amount of cleaning materials are used according to the analyzed sensory data and the output data received from the processing subsystem, hence for many users identified in sort time (e.g. more than 50 users per hour) a more intensive cleaning procedure is activated (e.g. more cleaning cycles with more effective cleaning materials), while for few identified users (e.g. less than 10 users in 10 hours) a less intensive cleaning procedure is activated.

Alternatively or in combination, the processing subsystem may comprise logic such as gate array logic to perform one or more logic steps.

The processing subsystem 206 can execute a sequence of machine-readable instructions, which can be embodied in a program or software. The instructions may be stored in a memory location.

The illumination device can comprise a light source 252. The light source can be of any type (e.g. laser or light-emitting diode) known in the art appropriate for the measurements to be made. In some embodiments, the light source emits from 350 nm to 1100 nm or more. The wavelength(s) and intensity of the light source will depend on the particular use to which the device 100 will be put. In some embodiments, the light source emits from 0.1 mW to 500 mW. In some cases, the illumination source may be a laser illumination source.

In some embodiments, the light source can comprise one or more light emitting diodes (LED). In some embodiments, the light source comprises a blue LED. In some embodiments, the light source comprises a red or green LED or an infrared LED.

The light source 252 can be mounted on a mounting fixture. In some embodiments, the mounting fixture comprises a ceramic package. For example, the light fixture can be a flip-chip LED die mounted on a ceramic package. The mounting fixture can be attached to a flexible printed circuit board (PCB) which can optionally be mounted on a stiffener to reduce movement of the illumination module.

The wavelength of the light produced by the light source 252 can be shifted by a shifting unit.

In some embodiments, the illumination device 250 is configured to transmit light and the sensing subsystem 260 is configured to receive light reflected from objects in the scene. In some embodiments, the system subsystems can be configured such that light can be transmitted from one unit to an object and reflected or scattered to another module that receives the light.

According to some embodiments, the treatment subsystem 260 comprises a spraying system 261 comprising one or more spraying devices 262, such as nozzles shaped for example as an elongated pipe. In some cases, the spraying devices may be positioned externally to or in the treatment module 260 and are configured to rotate perpendicular to the treatment module length. In some cases, the spraying devices 262 are configured to deliver and disperse cleaning material, such as materials including sanitization agents from one or more containers 242 and spray automatically and/or autonomously the materials, using for example one or more pumps 263 and pipes on the one or more objects or surfaces.

The spraying devices 262 are configured and enabled to operate one or more actions according to the data as analyzed and processed by the processing subsystem 206. According to some embodiments, the spraying devices may include one or more robotic arms, wheels, cogwheels.

In many embodiments, system 200 may also include a power source 280 (e.g. a battery or power supply). In some embodiments, the system 200 may be powered by a power supply from an external device. In some embodiments, the system has an independent power supply. In some embodiments, the power source may be independently charged, using, for example, external sources, and/or solar energy means.

In some embodiments, the system is configured and enabled to move horizontally and/or vertically using one or more motors. For example, the system may include one or more motors 211 connected to one or more wheels 212 or elevation units, such as wings 213 or propeller for enabling the system 100 to move in the scene or fly in the scene allowing the system to sense the scene as it moves and/or fly, as illustrated in FIG. 1D. In some cases, system 200 may be mounted or connected to a mobile machine such as a vehicle or drone to enable the device to move in all directions in the scene.

As mentioned hereinabove the system 200 may be in communication with a cloud-based server or storage device. System 200 is configured to acquire and analyze data such as sensory data of the scene and/or objects in the scene for example in real-time. The data may be related to one or more material, to determine the identity and/or additional properties of the material.

In many embodiments, system 200 may comprise a computing device configured to operate various aspects of data acquisition, transfer, analysis, storage, and/or display. The computer device typically comprises a central processing unit (also "processor" or the processing unit 206 herein), a memory, and a communication interface (also "communication circuitry" herein). The processor can execute a sequence of machine-readable instructions, which can be embodied in a program or software. The instructions may be stored in a memory location. Each subsystem of the device may communicate with one or more of the other subsystems of the device via the communication interface.

In many cases, the control board 232 may also be connected to a user interface 210. The user interface 210 may include input devices, output devices, and software routines configured to allow a user to interact with the control board. Such input and output devices respectively include but are not limited to, a display, a speaker, a keypad, a directional pad, a directional knob, a microphone, a touch screen, and the like.

The microphone facilitates the capturing of sound (e.g. voice commands) and converting the captured sound into electrical signals. In some cases, the electrical signals may be used by the onboard computer interface with various applications.

Figure 3:
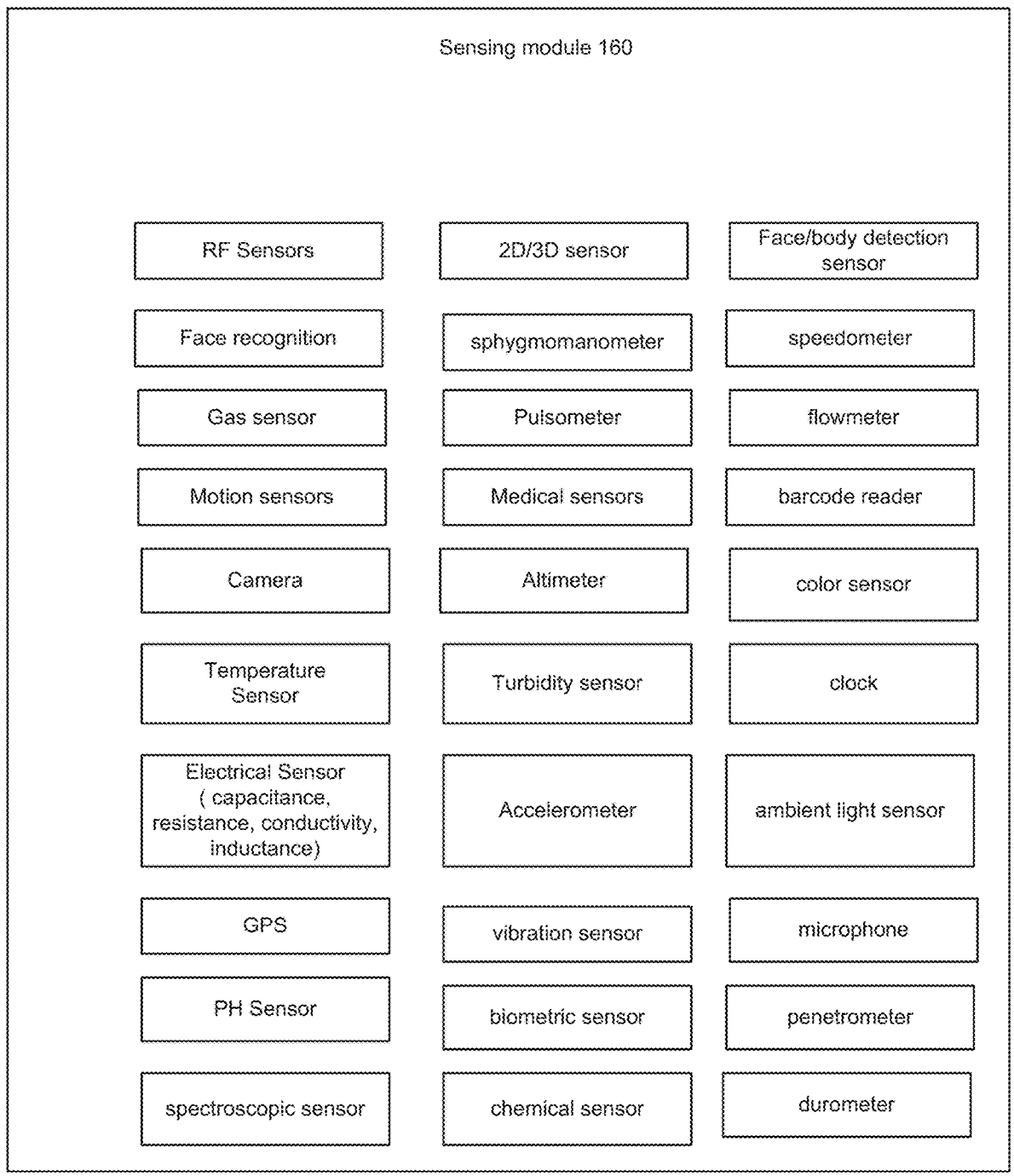
FIG. 3 shows a schematic diagram of a sensing subsystem, in accordance with some embodiments of the present disclosure.

FIG. 3 shows a schematic diagram of the sensing subsystem 260 of FIG. 2, in accordance with embodiments. The sensor subsystem 260 can be configured to obtain and/or measure information relating to one or more objects in a scene and/or one or more sample materials or elements in the scene and/or the scene.

In some cases, the sensor subsystem 260 can enable the identification of one or more objects in a scene and/or one or more sample materials based on multiple types of information measured by multiple types of sensors. Such multiple information devices may enhance the accuracy of detection or identification of the materials and objects.

The sensor elements of sensor module 260 may comprise any sensor configured to generate one or more signals associated with at least one aspect of the environment (e.g. scene), including the material/object/user being analyzed. For example, the sensor element may comprise one or more of a camera, temperature sensor, electrical sensor (capacitance, resistance, conductivity, inductance), altimeter, GPS unit, turbidity sensor, pH sensor, spectroscopic sensor, accelerometer, vibration sensor, biometric sensor, chemical sensor, color sensor, clock, ambient light sensor, microphone, penetrometer, durometer, barcode reader, flowmeter, speedometer, magnetometer.

In some cases, the type of sensors included or used by the device will depend on the particular use of the device (e.g. where the device will be placed (elevator; ATM, etc.)).

According to some embodiment, the sensing subsystem 260 comprises, one or more of the following sensors: medical sensors including, for example, one or more sensors for monitoring and diagnosing the object (e.g. which is suspected to include microbes) based on for example predefined or received database stored for example on storage and memory units 207. The medical sensors may include one or more pulsometer; sphygmomanometer; a sensor for detecting and/or diagnosing diseases, PH sensors; location sensors, including for example GPS means; voice sensors; speakers; motion sensors; gas sensors; sensors configured to identify hazardous materials and/or material of different types for example detection and diagnosing of substances such as infectors, drugs, explosive or toxic compounds and the like; face recognition sensors and methods; sensors configured to identify objects such as the type of a tool (e.g. driller) and the way the tool is operated; one or more cameras configured to capture an image of the scene and provide mapping data of the scene, for example using 2D or 3D cameras; RF sensors; temperature sensors.

The output of the sensor subsystem 260 may be associated with the output of other subsystems of the system, such as the illumination subsystem via at least one processing subsystem of the system. The processing subsystem may be configured to receive the outputs of the sensors in the sensing subsystem 260 and/or other units, analyze the outputs, and based on the analysis provide information (e.g. detailed and complete data) relating to at least one characteristic of one or more objects or materials in the scene for example to a display unit. A display subsystem may be provided on the system to allow the display of such information or on the user's mobile display.

In some embodiments, the measurement of the sample is performed using scattered ambient light.

In some cases, the diagnostic process of materials may be operated by obtaining one or more samples using, for example, the mechanical subsystem.

In some cases, the diagnostic process may be operated by visually imaging the materials or samples of the materials and further analyzing the images to identify and/or yield information on the materials including for example one or more of: type, amount, size weight, dimensions. In some embodiments, the images are analyzed using one or more of the following methods: Wavelets Gabor, PCA, LDA or a combination thereof.

In some cases, system 200 comprises a testing device for testing for example bacterium.

Figure 4:
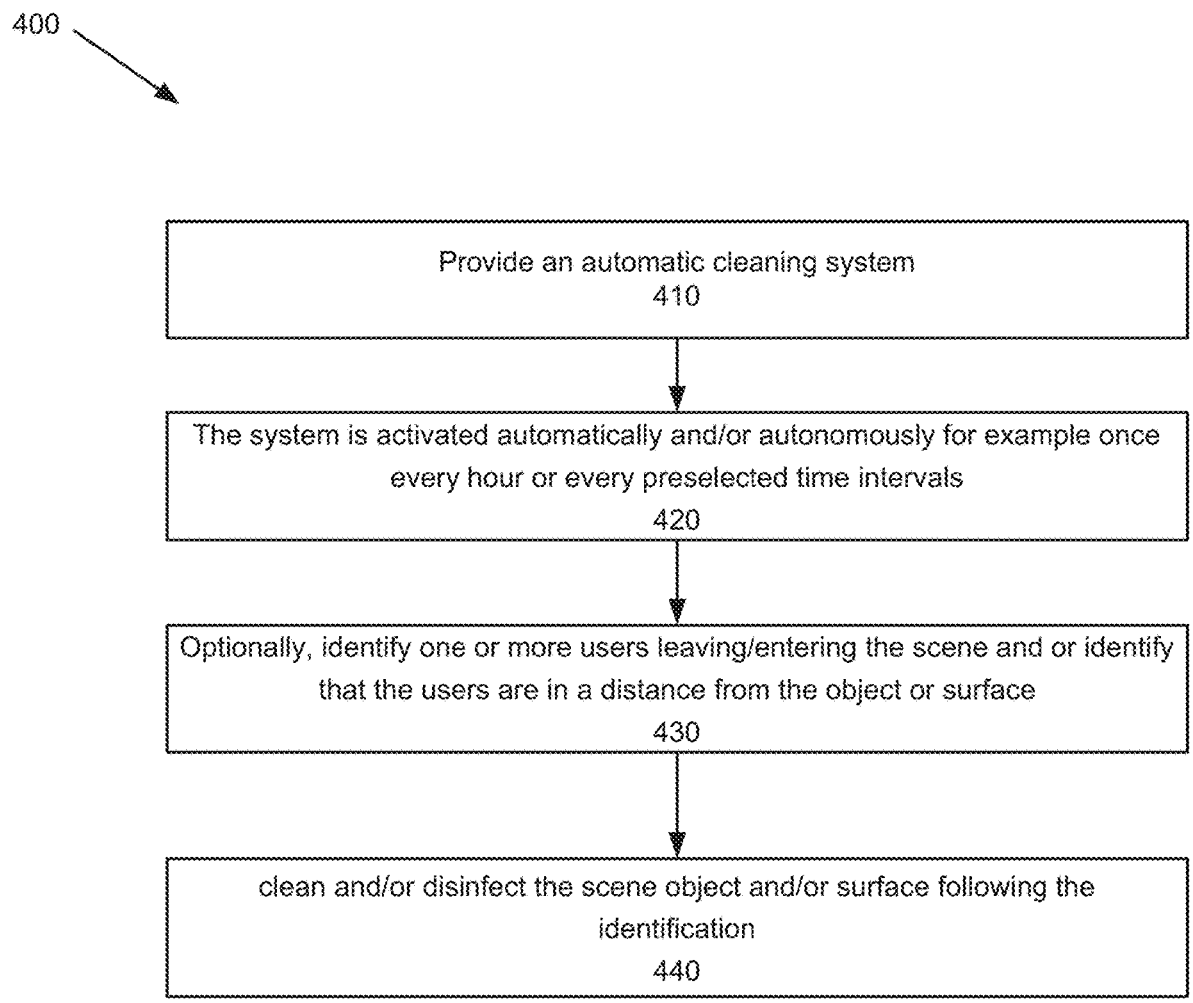
FIG. 4 shows a flowchart of a method for disinfecting or cleaning objects or surfaces in a scene using an automatic cleaning system, in accordance with embodiments.

FIG. 4 shows a flowchart of a method 400 for disinfecting or cleaning objects or surfaces in a scene using an automatic cleaning system such as system 100, in accordance with embodiments.

Some stages of method 400 may be carried out at least partially by at least one computer processor, e.g., by processor of a client device and/or system computing subsystem such as processor 145. Respective computer program products may be provided, which comprise a computer-readable storage medium having computer-readable program embodied therewith and configured to carry out of the relevant stages of method 400. In other embodiments, the method includes different or additional steps than those described in conjunction with FIG. 4. Additionally, in various embodiments, steps of the method may be performed in different orders than the order described in conjunction with FIG. 4

At step 410 a system such as system 100 or system 200 illustrated in FIGS. 1A-1E or 2 is provided and initially installed. At step 420 the system is activated automatically and/or autonomously for example once every hour or every preselected time intervals using a timer or scheduler such as scheduler 143 or any automatic device for automatically activating system 100 or system 200. In some embodiments, the schedular 143 or a processing subsystem or a clock activates the system for a predefined time and cleaning and/or disinfection procedure is activated, including for example cleaning and/or disinfecting the scene or one or more objects in the scene using cleaning material. In some cases, the cleaning procedure may be activated by one or more cleaning subsystems which accordingly activates the sparing nozzles for cleaning the scene and/or objects in the scene. Optionally, at step 430 a sensor such as the proximity sensor may identify that the one or more users are no longer at the scene and/or that the users plan to enter the scene again or touch objects or surfaces at the scene and at step 440 the system 100 may accordingly automatically or autonomously activate a second cleaning procedure for cleaning and/or disinfecting and/or sanitizing the scene. In some cases, steps 420-440 are repeated 1, 2, 3 or more times each hour. In some cases, the device may be activated by the user.

In some cases, if the sensors do not identify any user in the scene or near the scene (0-1 meter from the scene), for example for 12 hours a cleaning procedure will not be activated till one or more users are identified (e.g. to avoid waste of cleaning materials and as typically bacterium result from users use, etc.).

In some cases, where many users are identified, for example, around 50 or more users per hour the treatment will be accordingly be activated every minute and/or each time a user is identified.

Figure 5:
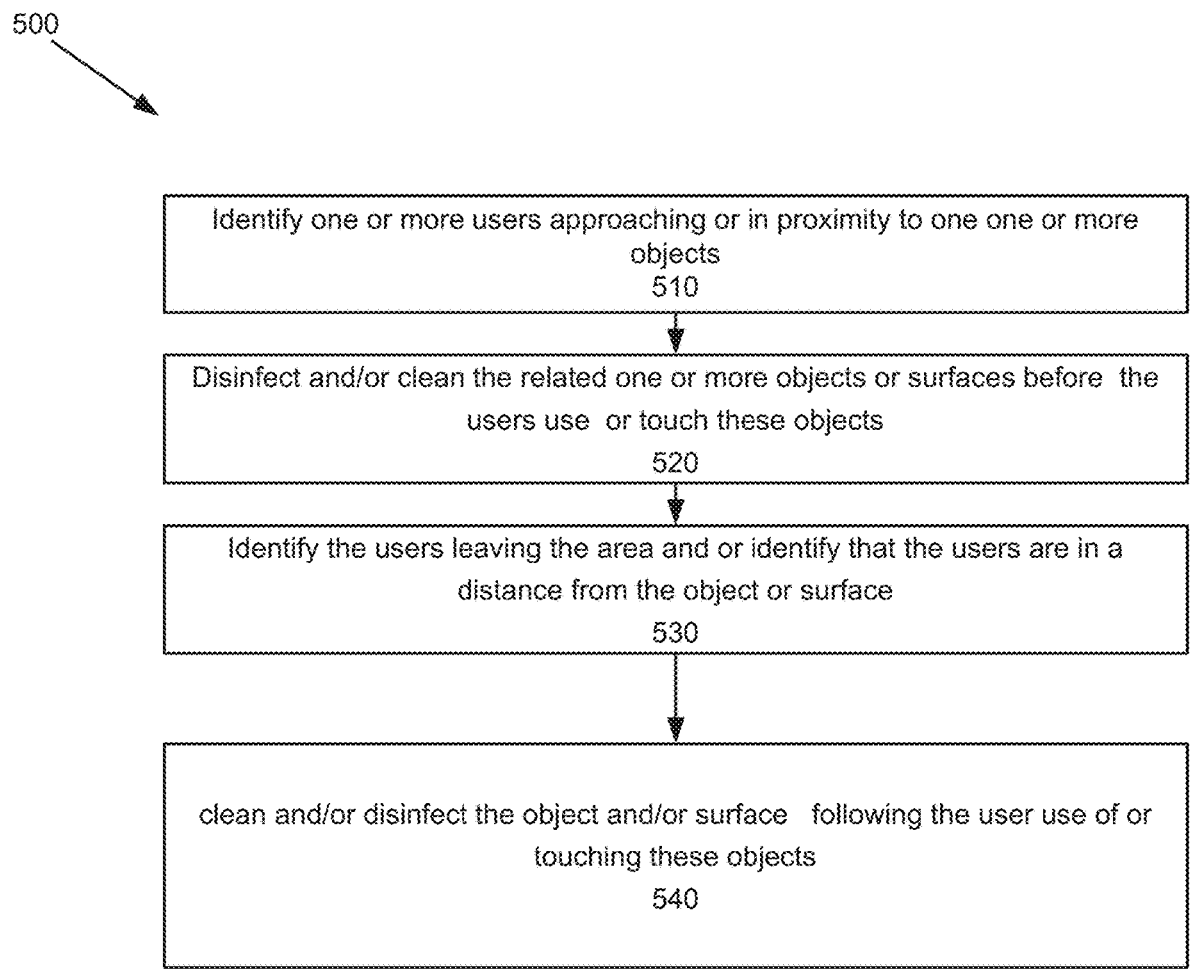
FIG. 5 shows a flowchart of a method for disinfecting or cleaning objects or surfaces in a scene, in accordance with some embodiments of the present disclosure.

FIG. 5 shows a flowchart of a method 500 for automatically and/or autonomously disinfecting or cleaning objects or surfaces in a scene using an automatic cleaning system such as system 100, in accordance with embodiments.

Some stages of method 500 may be carried out at least partially by at least one computer processor, e.g., by processor of a client device and/or system computing subsystem such as processor 145. Respective computer program products may be provided, which comprise a computer-readable storage medium having computer-readable program embodied therewith and configured to carry out of the relevant stages of method 500. In other embodiments, the method includes different or additional steps than those described in conjunction with FIG. 5. Additionally, in various embodiments, steps of the method may be performed in different orders than the order described in conjunction with FIG. 5.

At step 510, a system such as system 100 automatically and/or autonomously identifies one or more users such as users approaching or in proximity to one or more objects. For example, the users may be users which plan to use or touch the one or more objects or elements in the scene and/or pressing buttons for example for few seconds or in predefined intervals as illustrated in FIGS. 1A-1D. The users may be identified using one or more sensors such as the proximity sensor 125 which is configured and enabled to detect one or more users who are located at a distance 'd' from the system wherein 'd' may be in the range of around 1, 2, 3, 4, 5, 6, 7, 8, 9, 10, 20, 30, 40, 50, 60, 70, 80, 90, 100, 200, 300, 400, 500 cm or more. Following the identification of the user at step 520 the system disinfects and/or cleans the related one or more objects or surfaces and/or the area surrounding the objects and/or surfaces (e.g. 0-1 meter or more away from the objects). In accordance with embodiments, the system disinfects and/or cleans the related one or more objects before the user is too close or touches the related one or more objects or surfaces and/or the area surrounding the objects so the user will not be disturbed by the cleaning process.

In some cases, the user or users may be identified using one or more cameras and/or sensors such as temperature sensor and/or optic sensor and/or proximity sensor such as the proximity sensor 125 and/or the laser sensor 135. In some cases, the images captured by the one or more cameras may be analyzed to identify the users or objects on the users such as the user watch or mobile device and accordingly once identify activate the system for cleaning the related one or more objects or surfaces and/or the area surrounding the objects so the user will not be disturbed by the cleaning process At step 530 the one or more users are identified leaving the area, for example, going away or located at distance (e.g. 20-100 cm or more away from the objects) from the object and/or surface and at step 540 cleaning and/or disinfection is repeated (e.g. following the user use of or touching these objects). In some cases, the disinfection and/or cleaning may be automatically or autonomously be operated every hour and/or according to predefined time intervals and/or upon specific requests. In some cases, the disinfection and/or cleaning may be repeated until complete and optimal disinfection and/or cleaning is accomplished. In some cases, the disinfection and/or cleaning is repeated each time a user is identified approaching the surface or object and/or each time a user is identified leaving the area surrounding the surface.

Figure 6A:
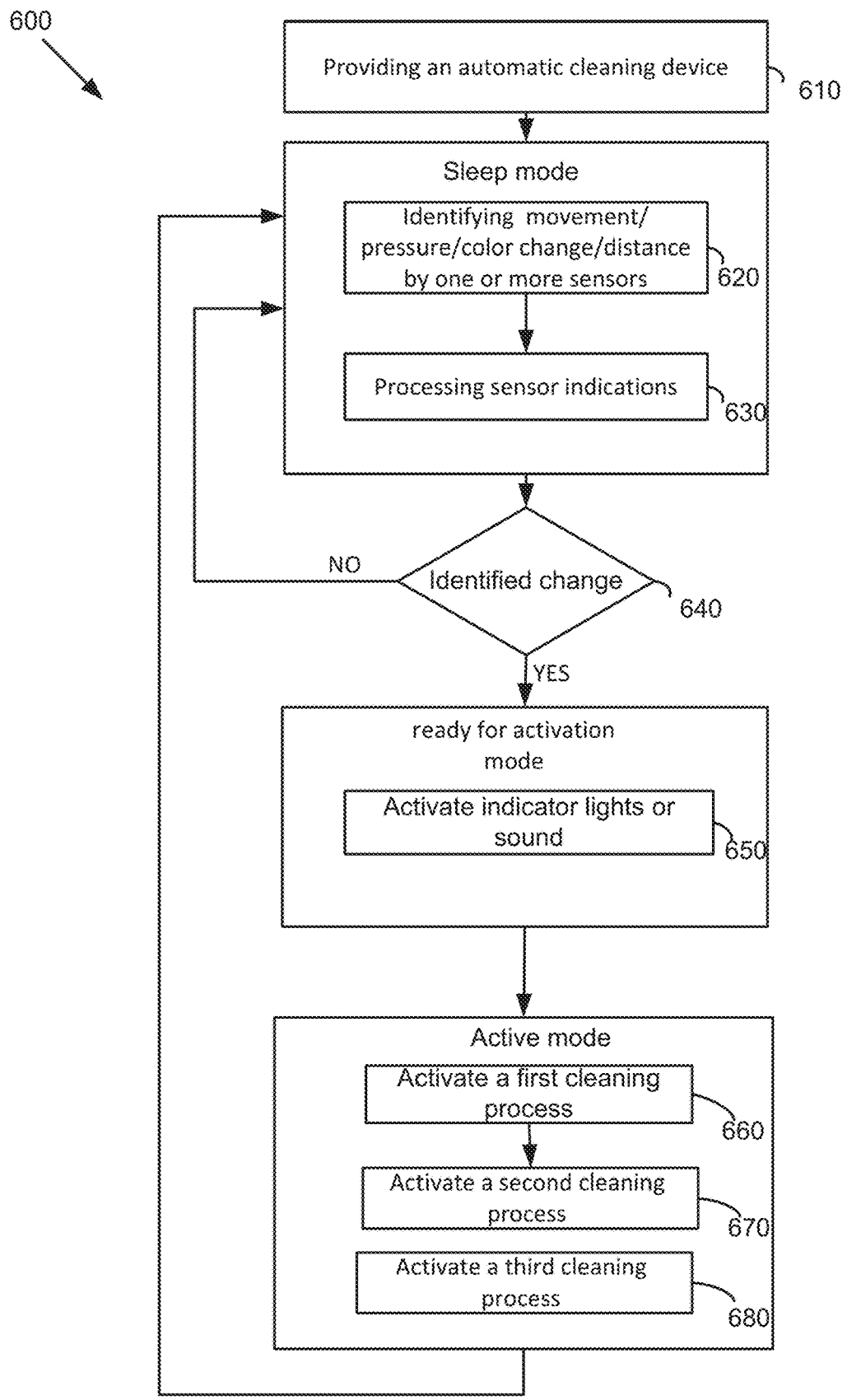
FIG. 6A illustrates a flowchart of a method for automatically and/or autonomously cleaning and/or foaming and/or disinfecting objects, in accordance with embodiments, in accordance with some embodiments of the present disclosure.

Reference is now made to FIG. 6A illustrates a flowchart of a method 600 for automatically and/or autonomously cleaning and/or foaming and/or disinfecting objects or surfaces, in accordance with embodiments.

Some stages of method 600 may be carried out at least partially by at least one computer processor, e.g., by processor of a client device and/or system computing subsystem such as processor 145. Respective computer program products may be provided, which comprise a computer-readable storage medium having computer-readable program embodied therewith and configured to carry out of the relevant stages of method 600. In other embodiments, the method includes different or additional steps than those described in conjunction with FIG. 6A. Additionally, in various embodiments, steps of the method may be performed in different orders than the order described in conjunction with FIG. 6A.

At step 610 cleaning systems such as system 100 or system 200 illustrated, accordingly, in FIGS. 1A-1E or FIG. 2 are provided and initially installed in a scene or on one or more objects in the scene, e.g. near an elevator's buttons or steering wheel (for example 1, 2, 3, 4, 5, 6, 7, 8, 9.10 cm or more from the objects in the scene). Typically, the system's initial state or 'default' state is 'sleep mode' where the system is inactivated or in a low power mode. In some cases, for indicating the specific state of the system one or more control lights may be operated, for example, according to the color of the lights (e.g. green—'active'-red 'inactive'). At step 620, one or more use indications are identified such as movement and/or pressure and/or distance and/or the voice and/or temperature and/or location and/or orientation of one or more users. According to some embodiments, the indications are monitored and identified, respectively, by one or more sensors, for example by an electronic pressure sensor and/or distance sensor and/or proximity sensor 125 and/or by a laser distance meter 153 and/or camera 155 and/or by a biologic sensor (e.g. PH sensors), and/or temperature sensor and/or a pressure detection sensor such as sensing module 160 of systems 100 or 200 for identifying and sensing pressure/movement/location/distance of the one or more users or by other types of sensors such as the sensors discussed hereinabove or other sensors as known in the art. The sensors are configured to identify the specific use and accordingly provide data (e.g. which includes one or more indications) to the processing subsystem which activates the treatment module based on the received data.

At step 630 the data (e.g. raw data such as specific indication such as movement, pressure or color, user movement and/or images) is analyzed by the processing subsystem and thereafter according to the processing output the device state transforms to a 'ready for activation' state or back to 'sleep mode'.

In accordance with embodiments, the processing subsystem is configured and enabled to analyze the captured sensory data, using one or more machine learning or network neural methods to yield detailed information including for example identification of the number of the one or more users approaching or in proximity to the one or more objects or surfaces or leaving the scene and/or the time the one or more users are at the scene and accordingly activate deactivate the one or more spraying devices.

At the following conditional step 640 if affirmative, and it is determined by the one or more processing units that a cleaning process is required then the system transforms to 'activation' mode. If an indication was not found, the system mode transforms back to a sleep mode. In some cases, one or more indication lights are switched on to an activation light (e.g. green) and/or a voice hazard is activated according to the identified indication. For example, yellow-colored indication for the first cleaning procedure (as illustrated at step 660) and green color for the second procedure (as illustrated at step 670). At step 650, the device is activated and a cleaning procedure is initiated based on the processed data (e.g. detailed information).

The cleaning process includes, according to some embodiments, the following steps: At step 660 the spraying subsystem is activated and one or more spraying devices such as nozzle 172 and 174 automatically spray fluids such as fluids mixed with one or more treatment materials/cleaning agents which were stored at the treatment device. The spraying may include using pump means such as pump 160.

In some cases, one or more nozzles such as nozzle 172 and 174 automatically move and/or rotate along rail spraying fluid along with one or more treatment materials/cleaning agents that were stored at the treatment device.

According to some embodiments, the treatment materials/cleaning agents may include the following materials sprayed in the following order: a. cleaning and whiting materials b. anti-stick materials c. foamy materials d. coloring materials e. perfuming materials. It is noted that the cleaning procedure may include the use of other materials according to a different order.

The treatment materials may include for example one or more of chlorine, etheric oils, coloring materials, sanitization materials which include for example clean alcohol or other sanitization materials, for anti-stick materials a silicon or Teflon materials may be used.

In some cases, the cleaning process may last for predetermined time interval of for example 1, 2, 3, 4, 5, 6, 7, 8, 9, 10, 11, 12, 13, 14, 15, 16, 17, 18, 19 or 20 or more seconds.

In some cases, the cleaning process may be repeated according to a cleaning matrix, which includes a cleaning procedure as illustrated hereinabove.

According to some embodiments, the cleaning matrix may be activated according to information or data indications received from the one or more sensors illustrated in FIG. 3 and which are further analyzed and processed by the processing subsystem. The information may comprise images of the scene or objects or objects' surroundings or mapping of the scene or RF data, radar data. According to some embodiments, the various information received from the multiple sensors may be used for proving a complete picture of the scene, and the cleaning matrix is generated based on this information. In some cases, the cleaning matrix is generated based on the processed sensory data.

In some cases where the image of the user or other object is incomplete, the processing subsystem may retrieve information from other sensors such as the RF sensor or the temperature sensor to identify and complete the needed data so almost complete and detailed information may be received on the scene. In some cases, the information may include data on the users, and/or objects and/or virus, bacterium found and identified in the scene. In some cases, the various data collected from some or all sensors is sliced to provide and summarize the data on the users or objects.

In some cases, the cleaning matrix may comprise dividing the scene into several sections (2, 3, 4, 5, 6, 7, 8, 9, 10 or more square cm sections) represented by the cleaning matrix and the processing steps may include identifying one or more specific sections of the matrix sections which require additional or specific treatment according to the identified status of the section. Once the sensory data (e.g. data obtained by the various sensors) processed (e.g. based on image processing, or RF data, radar data) the cleaning matrix may include data including which type of cleaning is needed for each section. In some cases, the cleaning matrix is based on the detailed data (e.g. the processed raw data) and the cleaning procedures as activated in steps 660 or the following steps 670 and 680 match the information provided by the processing subsystem, hence for many users identified in a short time (e.g. more than 50 users per hour) a more intensive cleaning procedure is activated (e.g. more cleaning cycles with more effective cleaning materials such as all cleaning steps 660, 670 and 680 are activated), while for few identified users (e.g. less than 10 users in 10 hours) a less intensive cleaning procedure is activated (e.g. only one cleaning cycle).

At step 670, following the activation of the spraying subsystem and/or once the first cleaning process is completed (for example after 8 seconds) a second cleaning process is initiated which typically comprises a sanitization procedure. According to some embodiments, the second cleaning process is executed by a first spraying subsystem or by and/or external arm to spray sanitation materials to the object and/or the object surface thus providing a complete and optimal cleaning and sanitation result in minimum time.

It is noted that the first cleaning process (step 660) and/or the second cleaning process (step 670) is typically initiated once the sensors (such as the proximity sensors) confirm that the user or any person is not in the vicinity of the treatment device 100, for example, based on an indication of a movement of the user or other indications confirming that the user is not in the area. Additionally, the second cleaning process (step 670) which comprises one or more sanitization procedures is activated once an indication is received confirming that the user or any person is no longer in the scene).

In some cases, one or more indications such as the user movement, voice, color or the movement are categorized and/or prioritized for example by the one or more processing subsystems to provide a secured and healthy cleaning process and avoid injuries to the user.

Optionally, at step 680 a third cleaning process may be automatically and/or cyclically activated, for example, each hour once the indicators confirm that there isn't any person in proximity to the scene or the treatment device. The third cleaning process may include the disinfection of the scene or objects for example by spraying subsystems or nozzles. Specifically, the disinfection comprises spraying a sanitizer which may volatilize in less than for example a few seconds followed by perfuming the object surroundings.

In some cases, the first and/or second or any cleaning process may be autonomously stopped or repeated according to indications received by the one or more sensors of the device or by external indications received at the processing subsystem. For example, the proximity sensor may send an indication that a user is still at the vicinity of the scene and therefore the processing subsystem will block any cleaning procedure or a cleaning procedure that might risk the user.

Alternatively or in combination, the processing subsystem may operate a cleaning procedure that will not risk the user (e.g. using only clean water). Alternatively or in combination, the processing subsystem may receive data, for example by the communication module not to clean the scene.

Figure 6B:
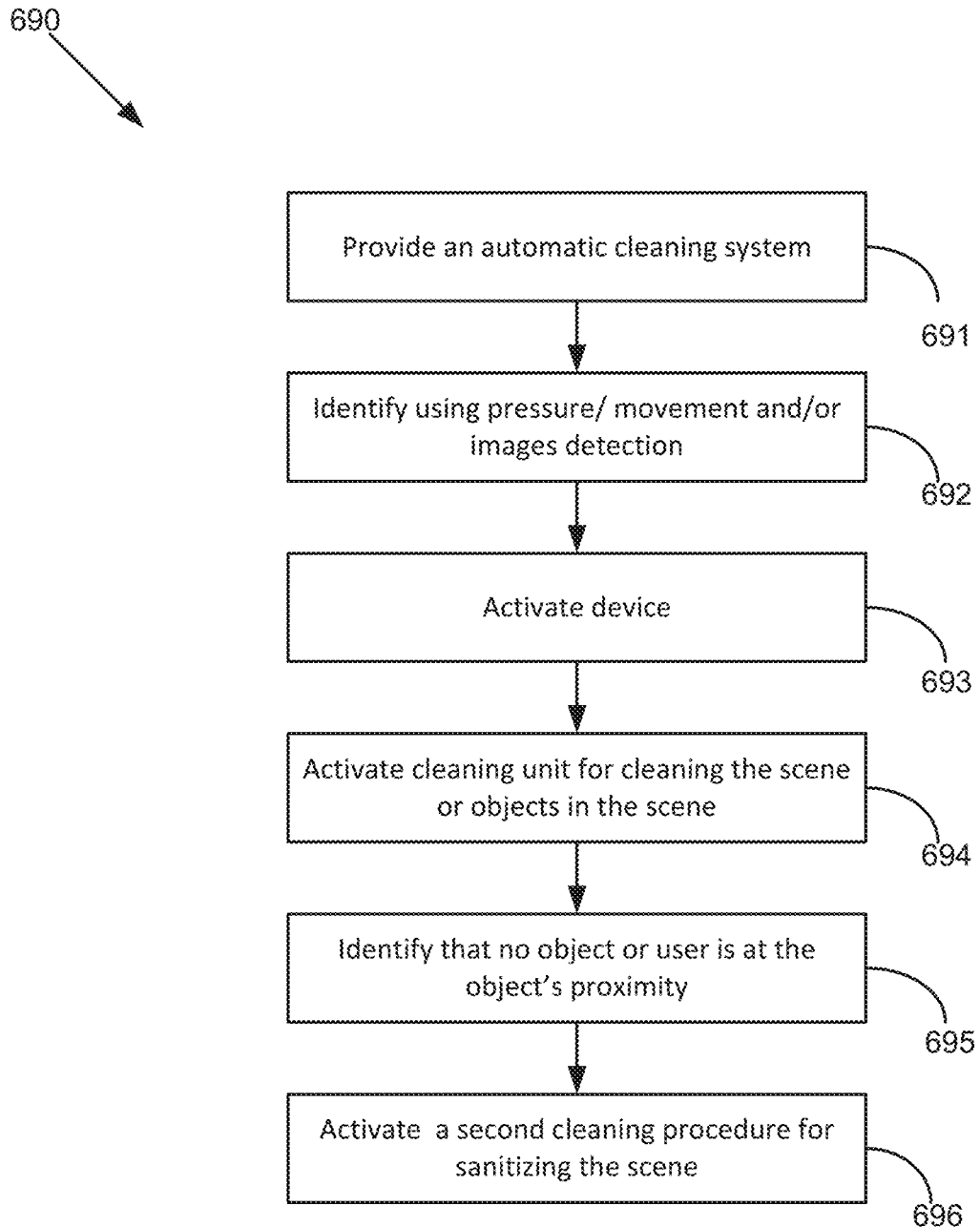
FIG. 6B is a flowchart of a method automatically and/or autonomously cleaning and/or foaming and/or disinfecting objects and/or surfaces, in accordance with embodiments.

FIG. 6B is a flowchart of a method 690 automatically and/or autonomously cleaning and/or foaming and/or disinfecting objects and/or surfaces, in accordance with another embodiment.

Some stages of method 690 may be carried out at least partially by at least one computer processor, e.g., by processor of a client device and/or system computing subsystem such as processor 145. Respective computer program products may be provided, which comprise a computer-readable storage medium having computer-readable program embodied therewith and configured to carry out of the relevant stages of method 690. In other embodiments, the method includes different or additional steps than those described in conjunction with FIG. 6B. Additionally, in various embodiments, steps of the method may be performed in different orders than the order described in conjunction with FIG. 6B.

At step 691 a system such as the systems 100 or 200 illustrated in FIGS. 1A-1E or 2 are provided and initially installed. At step 692 a sensor, such as a proximity sensor or movement sensor configured to identify one or more users that are in proximity to the systems 100, 200 or a movement of the one or more users and/or objects. In some cases, one or more imagers may be used to image the users and further to identify the user and/or the user's one or more electronic devices such as his mobile device. e.g. smartphone and/or smartwatch electronic card. At step 693 the device is activated as a result of the identification. At step 694 a timer (e.g. scheduler 143) and/or a processing subsystem activates the system for a predefined time and cleaning and/or disinfection procedure is activated, including for example cleaning and/or disinfecting the scene or one or more objects in the scene using cleaning material. In some cases, the cleaning procedure may be activated by the treatment subsystem which includes one or more cleaning subsystems (e.g. cleaning devices) which accordingly activates the sparing nozzles for cleaning the scene and/or objects in the scene. At step 695 a sensor such as the proximity sensor may identify that a user or that an object is no longer at the scene and at step 696 a timer (e.g. scheduler 143) or the processing subsystem may accordingly activate a second cleaning procedure for sanitizing the scene.

Figure 7:
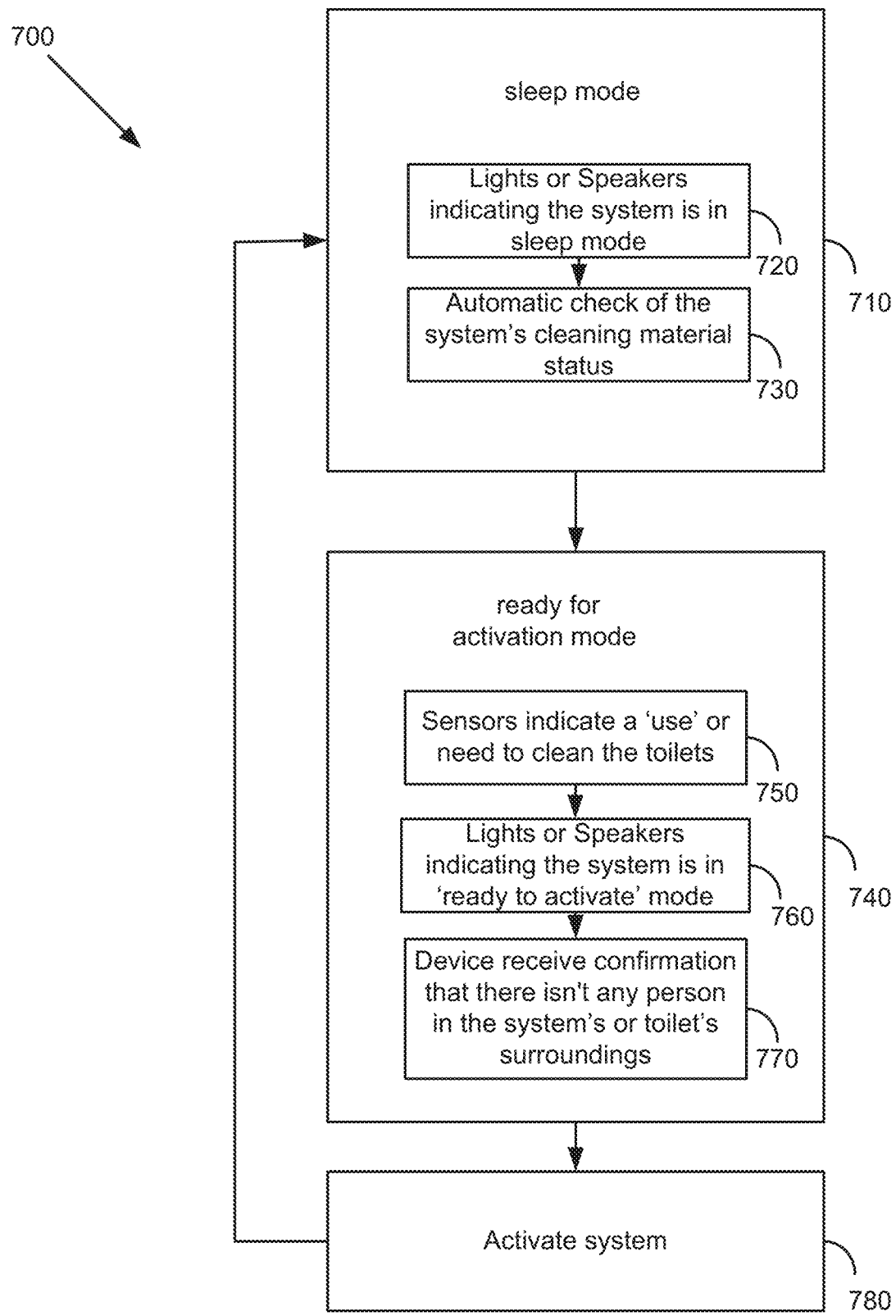
FIG. 7 is a flow chart illustrating in detail a process of operating the cleaning devices, in accordance with some embodiments of the present disclosure.

FIG. 7 is a flow chart illustrating in detail a process 700 of operating cleaning systems such as systems 100 or 200, in accordance with embodiments.

Some stages of method 700 may be carried out at least partially by at least one computer processor, e.g., by processor of a client device and/or system computing subsystem such as processor 145. Respective computer program products may be provided, which comprise a computer-readable storage medium having computer-readable program embodied therewith and configured to carry out of the relevant stages of method 700. In other embodiments, the method includes different or additional steps than those described in conjunction with FIG. 7. Additionally, in various embodiments, steps of the method may be performed in different orders than the order described in conjunction with FIG. 7.

Prior to the system activation, the system is typically in sleep mode 710 where the system's subsystems are not operated or on energy-saving mode. At step 720 one or more indication lights or speakers provide information of the system's status (e.g. according to the indicator light color, or upon pushing a status indication button), confirming that the system will not be activated. In some cases, at step 730 the system may periodically operate an automatic check of the system's cleaning material status. Accordingly, the material containers may be automatically filled via one or more dedicated pipes and pumps connected to an external or an internal tank. Alternatively or in combination, the system's containers may be filled by a user. At step 740 the system's mode is transformed from 'sleep' mode to 'ready for activation' mode once one or more sensors such as the proximity sensors indicate at step 750 a use of the object. Accordingly, at step 760 lights or speakers indicate the system is in 'ready to activate' mode and at step 770, once the sensors confirm that that the one or more users are no longer in proximity to the object or at the scene, the system's processor automatically activates the system at step 780 to initiate a cleaning process as illustrated in FIG. 6A and FIG. 6B. For example, once the user leaves the scene the first cleaning process.

Further details on systems and methods for disinfecting or cleaning objects or surfaces in a scene may be found in U.S. Pat. No. 10,494,803 entitled "TOILET CLEANING DEVICES SYSTEMS AND METHODS" and PCT application number PCT/IL2019/050637 entitled "SYSTEMS DEVICES AND METHODS FOR DETECTING AND DIAGNOSING SUBSTANCES", the contents of which are incorporated herein by reference in their entirety.

In further embodiments, the processing subsystem may be a digital processing device including one or more hardware central processing subsystems (CPU) that carry out the device's functions. In still further embodiments, the digital processing device further comprises an operating device configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the device described herein. Those of skill in the art will also recognize that select televisions with optional computer network connectivity are suitable for use in the device described herein. Suitable tablet computers include those with booklet, slate, and convertible configurations, known to those of skill in the art.

In some embodiments, the digital processing device includes an operating device configured to perform executable instructions. The operating device is, for example, software, including programs and data, which manages the device's hardware and provides services for execution of applications. Those of skill in the art will recognize that suitable server operating devices include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating devices include, by way of non-limiting examples, Microsoft® Windows®, Apple® Mac OS X®, UNIX®, and UNIX-like operating devices such as GNU/Linux®. In some embodiments, the operating device is provided by cloud computing. Those of skill in the art will also recognize that suitable mobile smart phone operating devices include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, the device disclosed herein includes one or more non-transitory computer readable storage media encoded with a program including instructions executable by the operating device of an optionally networked digital processing device. In further embodiments, a computer readable storage medium is a tangible component of a digital processing device. In still further embodiments, a computer readable storage medium is optionally removable from a digital processing device.

In some embodiments, a computer readable storage medium includes, by way of non-limiting examples, CD-ROMs, DVDs, flash memory devices, solid state memory, magnetic disk drives, magnetic tape drives, optical disk drives, cloud computing devices and services, and the like. In some cases, the program and instructions are permanently, substantially permanently, semi-permanently, or non-transitorily encoded on the media. In some embodiments, the device disclosed herein includes at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof. In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, the device disclosed herein includes software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the device disclosed herein includes one or more databases, or use of the same. In view of the disclosure provided herein, those of skill in the art will recognize that many databases are suitable for storage and retrieval of information as described herein. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element. It is to be understood that where the specification states that a component, feature, structure, or characteristic "may", "might", "can" or "could" be included, that particular component, feature, structure, or characteristic is not required to be included. Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described. Methods of the present invention may be implemented by performing or completing manually, automatically, or a combination thereof, selected steps or tasks.

The descriptions, examples, methods and materials presented in the claims and the specification are not to be construed as limiting but rather as illustrative only. Meanings of technical and scientific terms used herein are to be commonly understood as by one of ordinary skill in the art to which the invention belongs, unless otherwise defined. The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for disinfecting one or more objects or surfaces in a scene, the system comprising:
    a sensing subsystem, the sensing subsystem comprising:
        at least one sensor configured and enabled to identify at least one user approaching the one or more objects or surfaces or the scene;
        at least one device for measuring a distance of said at least one user or said one or more objects or surfaces from the system;
        at least one timer for measuring the time said at least user or said one or more objects are in the scene or touching the one or more objects or surfaces;

a treatment subsystem, said treatment subsystem comprising:
one or more containers comprising cleaning or disinfecting agents or materials;
at least one pump connected via one or more pipes to the one or more containers said at least one pump is configured and enabled to pump said cleaning or disinfecting agents or materials to one or more spraying devices, wherein said one or more spraying devices comprising one or more nozzles for spraying the one or more objects on the scene or on the one or more objects or surfaces in the scene;
a processing subsystem comprising at east one processor, said at least one processor is configured to:
receive said identification of the at least one user approaching the one or more objects or surfaces or the scene;
activate the one or more spraying devices before or after the identified one or more users touch the one or more objects or surfaces or approach or leave the scene based on the measured time or identification or location or measured distance of the one or more users from the system.

2. The system of claim 1 wherein the at least one sensor is configured and enabled to capture sensory data of the scene and wherein the processing subsystem is configured to:
analyze the captured sensory data, using one or more machine learning or network neural methods to yield detailed information on the scene; and
accordingly activate or deactivate the one or more spraying devices.

3. The system of claim 2, wherein the detailed information comprises one or more of:
measuring the number of the one or more users approaching or in proximity to the one or more objects or surfaces in the scene or leaving the scene; the time the one or more users are at the scene; classification of the users; the type and amount of an identified bacterium.

4. The system of claim 3, comprising a scheduler wherein the scheduler is configured to schedule and activate the treatment subsystem based on the measured time or number of the one or more users identified in the scene or touching objects or surfaces in the scene or approaching or in proximity to the one or more objects or surfaces in the scene.

5. The system of claim 1, wherein the sensing subsystem comprises:
an illumination subsystem comprising at least one illumination source configured to illuminate the scene.

6. The system of claim 1, wherein said one or more nozzles are fog nozzles.

7. The device of claim 1, wherein the spraying devices may be positioned externally to or in the treatment subsystem and wherein the nozzles are configured to rotate in perpendicular to the treatment module length.

8. The system of claim 7, wherein the cleaning or disinfecting agents or materials are in the form of liquid or gas or any other aggregate state.

9. The system of claim 2, wherein the sensory data comprise one or more images of the scene.

10. The system of claim 1, wherein the disinfection or cleaning may be automatically or autonomously be operated every hour or according to predefined time intervals or upon specific requests.

11. The system of claim 1, wherein the sensing subsystem may include one or more sensors selected from the group consisting of:
proximity sensors; pressure sensors for detecting a movement of a user at the system's vicinity and accordingly activating or deactivating the system; RF sensors, IR sensors, pressure sensors, laser sensors.

12. The system of claim 1, comprising a communication circuitry to couple to the system and communicate with a remote server, and wherein the processing subsystem comprising instructions to transmit the sensory data to the remote server.

13. The system of claim 2, wherein the sensory data comprises one or more of an identification of the one or more objects, a classification of the one or more objects among a plurality of classifications, one or more components the one or more objects.

14. The system of claim 1, wherein the treatment subsystem comprises at least one robotic arm.

15. The system of claim 1, comprising a power source.

16. The system of claim 1, comprising one or more motors for enabling the system to move in the scene or fly in the scene.

17. The system of claim 1, wherein the system is attached to a mobile system said mobile system comprising a motor configured to move the system.

18. The system of claim 1, wherein the system is attached to a drone or a vehicle.

19. The system of claim 1, comprising one or more electronic faucet for controlling the quantity and timing of a disinfection process.

20. The system of claim 2, wherein the treatment subsystem is activated according to a cleaning matrix, said cleaning matrix comprises cleaning procedures and wherein the cleaning matrix is based on the processed sensory data.

* * * * *